(12) United States Patent
McMorrow et al.

(10) Patent No.: US 7,331,925 B2
(45) Date of Patent: Feb. 19, 2008

(54) SYSTEM FOR REMOTE EVALUATION OF ULTRASOUND INFORMATION OBTAINED BY A PROGRAMMED APPLICATION-SPECIFIC DATA COLLECTION DEVICE

(75) Inventors: Gerald J. McMorrow, Duvall, WA (US); William Barnard, Maple Valley, WA (US); Stephen Dudycha, Bothell, WA (US); Timothy Shelton, North Bend, WA (US); Vikram Chalana, Mill Creek, WA (US)

(73) Assignee: Verathon, Inc., Bothell, WA (US)

( * ) Notice: Subject to any disclaimer, the term of this patent is extended or adjusted under 35 U.S.C. 154(b) by 0 days.

(21) Appl. No.: 11/216,244

(22) Filed: Aug. 30, 2005

(65) Prior Publication Data

US 2005/0288584 A1 Dec. 29, 2005

Related U.S. Application Data

(63) Continuation-in-part of application No. 10/445,244, filed on May 23, 2003, now Pat. No. 7,189,205, which is a continuation of application No. 09/620,766, filed on Jul. 21, 2000, now Pat. No. 6,569,097.

(51) Int. Cl.
*A61B 8/00* (2006.01)
(52) U.S. Cl. .................................................. 600/437
(58) Field of Classification Search ................ 600/437, 600/443, 447, 453–456; 128/916; 705/2–4, 705/51–53; 709/217–219; 382/128
See application file for complete search history.

(56) References Cited

U.S. PATENT DOCUMENTS

| | | | | |
|---|---|---|---|---|
| 4,764,870 A * | 8/1988 | Haskin | ........................ | 348/443 |
| 5,291,401 A * | 3/1994 | Robinson | .................... | 382/132 |
| 5,715,823 A * | 2/1998 | Wood et al. | ................ | 600/437 |
| 5,897,498 A * | 4/1999 | Canfield et al. | ............ | 600/437 |
| 6,006,191 A * | 12/1999 | DiRienzo | ........................ | 705/2 |
| 6,101,407 A * | 8/2000 | Groezinger | ................. | 600/407 |
| 6,230,043 B1 * | 5/2001 | Johnson | ...................... | 600/425 |
| 6,322,505 B1 * | 11/2001 | Hossack et al. | ............ | 600/437 |
| 6,350,239 B1 * | 2/2002 | Ohad et al. | ................. | 600/437 |
| 6,418,334 B1 * | 7/2002 | Unger et al. | ................. | 600/407 |
| 6,440,071 B1 * | 8/2002 | Slayton et al. | ............... | 600/437 |
| 6,511,426 B1 * | 1/2003 | Hossack et al. | ............ | 600/437 |
| 6,526,304 B1 * | 2/2003 | Patel et al. | .................. | 600/407 |
| 6,569,097 B1 * | 5/2003 | McMorrow et al. | ........ | 600/437 |
| 6,621,918 B1 * | 9/2003 | Hu et al. | ..................... | 382/128 |
| 6,718,192 B1 * | 4/2004 | Samara et al. | .............. | 600/407 |
| 6,725,087 B1 * | 4/2004 | Rubinsky et al. | ........... | 600/547 |
| 6,931,270 B2 * | 8/2005 | Daft et al. | ................... | 600/407 |
| 7,189,205 B2 * | 3/2007 | McMorrow et al. | ........ | 600/437 |
| 2004/0030585 A1 * | 2/2004 | Sariel | ............................. | 705/3 |

* cited by examiner

Primary Examiner—Francis J. Jaworski
(74) Attorney, Agent, or Firm—Jensen & Puntigam, P.S.

(57) ABSTRACT

A system which includes at least one ultrasound data collection device which is programmable to carry out a specific ultrasound procedure on a selected part of a human body of a patient. The resulting ultrasound data is transmitted via a local server at the site of the data collection device to the internet and from there to a web database server which processes the raw ultrasound data to produce medical result information, including ultrasound images, which is then sent to a skilled technician, who accepts the results, rejects or edits them. Accepted medical results are transmitted back to the medical practitioner, while edited medical results are reprocessed, the results of which are transmitted to the medical practitioner.

6 Claims, 7 Drawing Sheets

SYSTEM FOR REMOTE EVALUATION OF ULTRASOUND INFORMATION OBTAINED BY A PROGRAMMED APPLICATION-SPECIFIC DATA COLLECTION DEVICE

PRIOR APPLICATION

This is a continuation-in-part application of U.S. patent application Ser. No. 10/445,244, filed on May 23, 2003, now U.S. Pat. No. 7,189,205, which was a continuation of Ser. No. 09/620,766, filed on Jul. 21, 2000, now U.S. Pat. No. 6,569,097, the priority of which is hereby claimed.

TECHNICAL FIELD

This invention relates generally to medical diagnostic systems using ultrasound, and more particularly concerns application-specific medical ultrasound systems.

BACKGROUND OF THE INVENTION

The majority of medical ultrasound examinations/procedures are carried out using "general purpose" ultrasound machines, which produce images of a selected portion of the human body. These images are in turn interpreted by a trained specialist in ultrasound. Radiologists, sonographers and, in some cases, specially trained physicians, usually in certain specialties, are among those who are trained to read and interpret an ultrasonic image. The cost of a general purpose ultrasound machine, however, is quite high, as is the cost of interpretation. Accordingly, an ultrasound procedure is typically quite expensive. This cost factor inherently limits the use of ultrasound, even though it is potentially a widely applicable, non-invasive diagnostic tool.

An alternative to the general purpose ultrasound machine is an application-specific ultrasound device. With an application-specific device, instead of using a general purpose ultrasound machine, a single type of ultrasound procedure is accomplished. There are many examples of application-specific or single purpose ultrasound machines. Two examples are shown in U.S. Pat. No. 4,926,871 and U.S. Pat. No. 5,235,985, both of which are directed toward a device for measuring the amount of urine in the bladder.

Instead of producing a real-time image which must be interpreted by a skilled operator, by measuring the image and then calculating the volume, the application-specific apparatus uses ultrasound signals and follow-on signal processing to automatically locate the bladder within the overall ultrasound volume, determine its boundaries, and then automatically compute the bladder volume, which is then provided to the trained, but not ultrasound skilled (e.g. sonographer), operator.

While bladder volume, of course, can be determined using a general purpose machine, as indicated above, an application-specific machine itself produces an actual volume number. This approach not only decreases the time to produce a bladder volume determination, it is also typically more accurate, and certainly less expensive. It does not require the services of an ultrasound-skilled operator, because the machine itself automatically produces the desired bladder volume information once the ultrasound probe (transmitter/receiver) has been properly positioned.

Application-specific ultrasound devices significantly lower the cost of ultrasound examinations and thus can be regularly used for a single patient in order to track bladder volume information over an extended period of time. This has proved to be extremely useful in both diagnosis and treatment of bladder dysfunction.

There are many other examples of application-specific ultrasound machines. These include machines which determine abdominal aorta size and kidney volume, among others. The significant disadvantage of application-specific ultrasound machines is that they are, in fact, just that—useful for just a single application. It would be too expensive and too cumbersome for a physician, particularly a general practitioner, to maintain a large number of application-specific ultrasound machines, even though ultrasound is useful in a variety of diagnostic situations.

Accordingly, it would be desirable to have an ultrasound system which is inexpensive, reliable and which does not require a specially trained operator and which further can be used in a variety of diagnostic situations.

SUMMARY OF THE INVENTION

Accordingly, the present invention is a system for generating application-specific medical ultrasound information, comprising: a local ultrasound data collection assembly to carry out an ultrasound scan of a selected part of the human body of a patient at a given location by an operator and to produce raw, substantially unprocessed ultrasound information therefrom; a data transmission system for transmitting said substantially unprocessed ultrasound information produced by the assembly to a processing location physically remote from the data collection assembly location; a processor at the remote location for automatically processing said transmitted information sufficiently to produce initial medical results comprising ultrasound images and/or a medical analysis of the selected body part from the raw ultrasound information, wherein the initial medical results are then transmitted to a sonographer who accepts the initial medical results, rejects it or decides to edit it, wherein if accepted, the initial medical results are transmitted back to a medical practitioner associated with the patient; and a display device for displaying the ultrasound images, having the capability of permitting a sonographer to take measurements of the ultrasound images and/or mark portions of the images to produce edited ultrasound images, wherein the edited ultrasound images are then transmitted back to the processor for another automatic processing thereof to produce further medical results, the further medical results then being transmitted back to the medical practitioner associated with the patient.

BEST MODE FOR CARRYING OUT THE INVENTION

Figure 1:
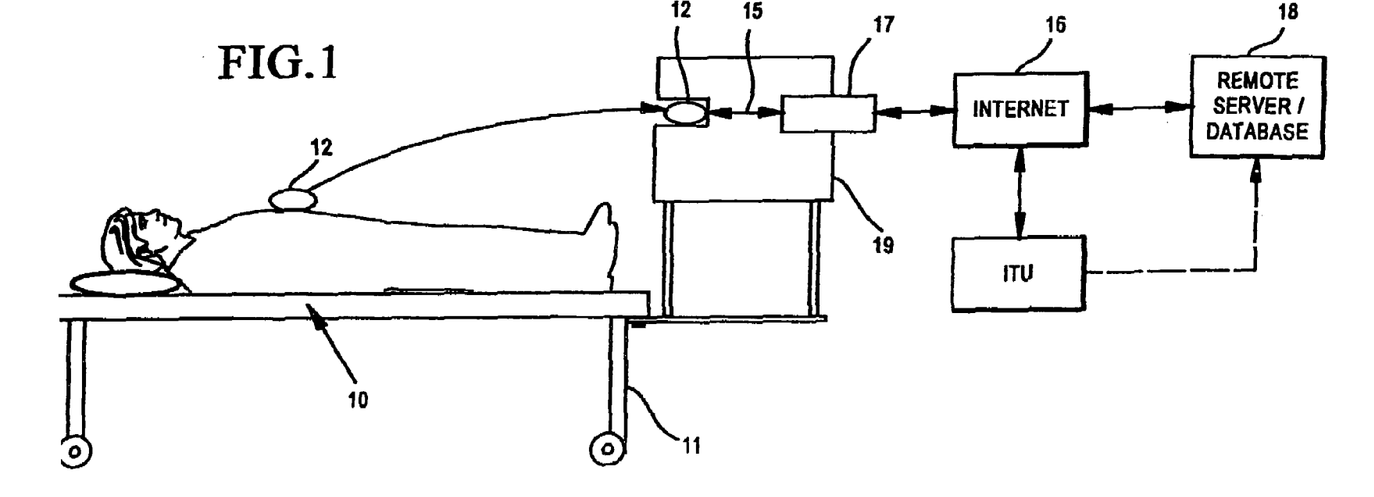
FIG. 1 is a diagram showing the complete system of the present invention.

FIG. 1 shows the overall system of the present invention. The patient upon whom the ultrasound procedure is to be performed is shown generally at 10. In FIG. 1, the patient is shown in a supine position on a table 11; however, the patient can be in virtually any position, depending upon the particular section of the body being imaged by the ultrasound device.

Figure 3:
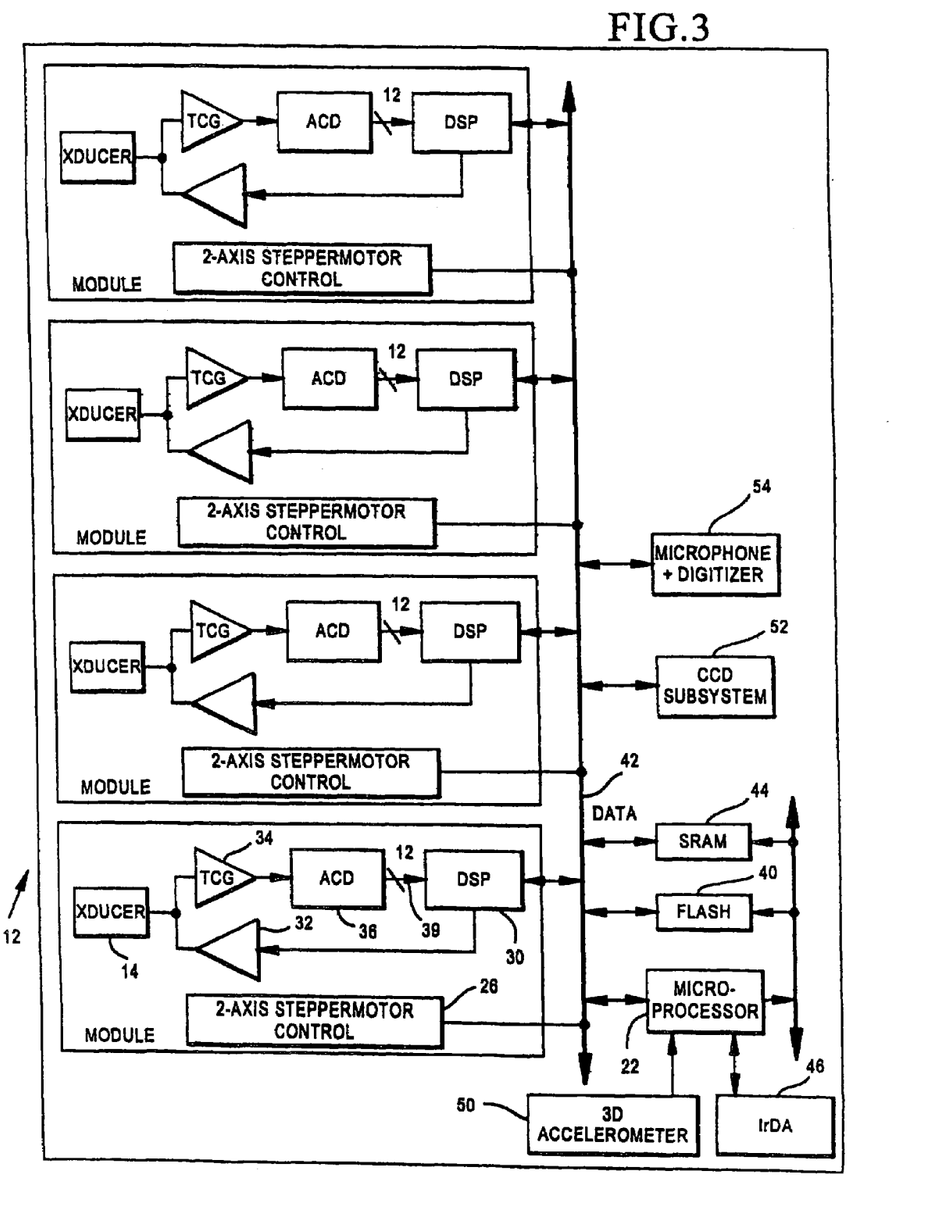
FIG. 3 is a diagram showing the block diagram of the data collection device portion of FIG. 1.

A data collection device (DCD) is shown generally at 12. DCD 12 includes a conventional ultrasound transducer (transmitter/receiver) 14 (FIG. 3). DCD 12 is programmed, as described below, to perform a specific ultrasound examination. In general, the operator places DCD 12 appropriately on the patient in the region which is to be imaged, and the ultrasound procedure is undertaken by the transmission and return of ultrasound signals. As an example, if the bladder is to be imaged, DCD 12 is placed on the skin area adjacent the bladder. The same procedure would be followed for other organs or areas of the body. The ultrasound information obtained by the DCD is then transmitted to a remote location where it is processed to produce a recognizable result of some kind, such as a three-dimensional model of the body part being imaged or specific numerical result.

More specifically, referring still to FIG. 1, DCD 12 is used in combination with an internet-connected "thin server" 17, linked to DCD 16 by a communication link 15. In one example, thin server 17 can be an off-the-shelf personal digital system (PDA). Alternatives to the PDA could include a conventional PC, laptop or other internet-accessible device. PDA 17 includes a conventional web browser and through the internet 16 can log onto a system ultrasound web database and server, generally indicated at 18. Web database and server 18 will, among other data, maintain a list of patients for the physician using the DCD and PDA combination.

Prior to beginning the ultrasound procedure, the patient is first identified to the PDA. If the patient is not in the web database 18, information about the patient will be created in the form of a record for storage in web database 18. PDA 17 will then display a list of application-specific programs for possible use by the data collection device 12. The selected program will then control the operation of the DCD for a specific ultrasound application.

The operator will select one from the list of programs available, which will then be downloaded into the data collection device 12. The communication link 15 between DCD 12 and PDA 17 can be either hard wire or wireless, such as infrared. In the event that infrared is used, DCD 12 and PDA 17 will be placed in a rack or stand 19 which will align the two devices appropriately for a line-of-sight Ir infrared transmission. The specific selected program selection is then transmitted through PDA 17 from the system database 18 through the internet.

DCD 12 may vary in shape, depending upon the surface of the body on which it is used, particularly whether it is to be used internally, such as vaginally, or externally, such as on the chest or abdominal area. DCD 12 in the embodiment shown is battery-powered and quite rugged in construction and will be operated by a simple on-off switch or pushbutton.

The DCD includes a spherical coordinate control module for the ultrasound transducer. The control module includes two stepper motors working in combination that will sweep the ultrasound transducer (and the ultrasound signals) through a three-dimensional volume.

Figures 1A, 2:
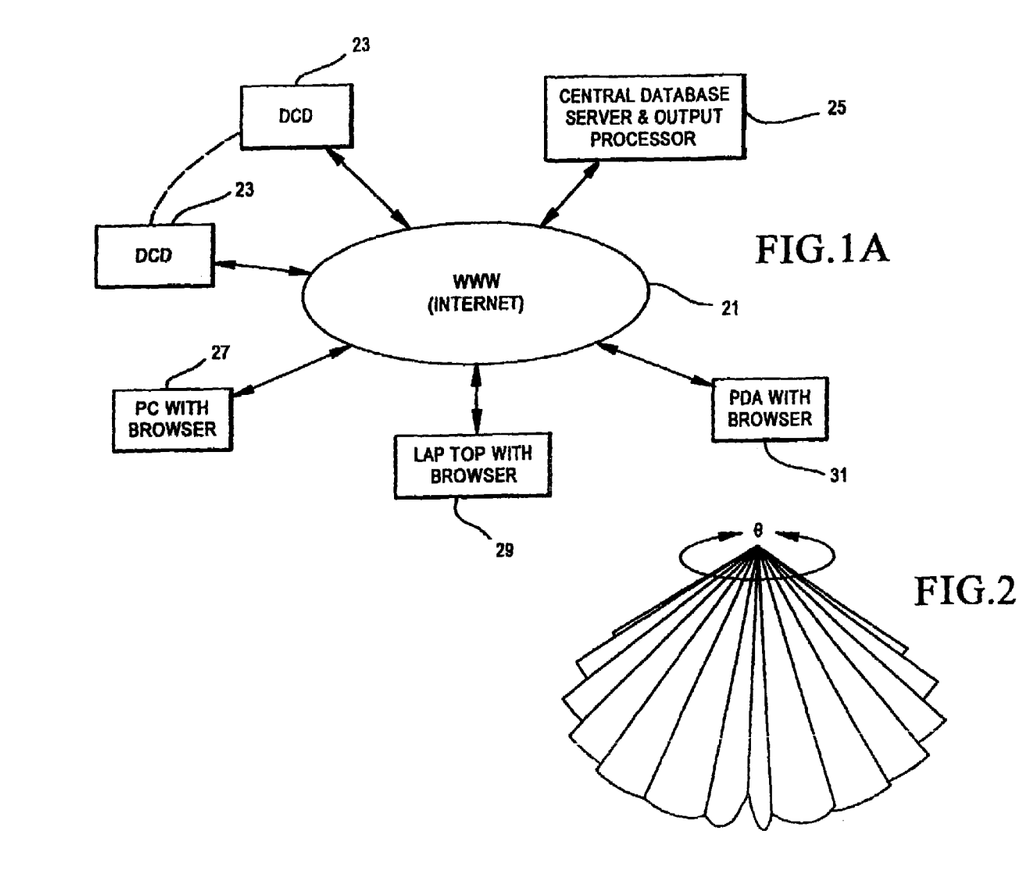
FIG. 1A is a diagram illustrating the overall system of the present invention.
FIG. 2 is a diagram showing the ultrasound coverage of the transducer portion of the system of FIG. 1.

Referring to FIGS. 2 and 3, DCD 12 includes a microprocessor 22 which controls the movement of the transducer 14 through a two-axis stepper motor control 26, which is used to step the transducer through a three-dimensional volume in precise movements. One motor (not shown) moves the transducer 14 through a specific angle in a given plane, referred to as the phi ($\phi$) dimension (FIG. 2). This angle can be varied, but in the embodiment shown is 120°. Approximately 77 ultrasound signals are transmitted in the embodiment shown as the transducer is moved through the 120° angle in one phi plane. This could differ; in another embodiment, the number of ultrasound signals could be up to 120.

After the ultrasound signal sweep in the one phi plane is made, a second motor (not shown) moves the transducer in the theta ($\theta$) direction, shown in FIG. 2. The transducer 14 is then again swept through a 120° angle phi plane. This process continues until the transducer has completed a 360° theta coverage. While in some cases it may not be necessary to complete a 360° coverage, the system of the present invention has the ability to do so. In the embodiment shown, successive scan lines are separated by 1.5°, although this can be readily varied. The resulting three-dimensional ultrasound "cone" coverage is shown in FIG. 2. It should be understood, however, that other coverage patterns can be successfully used, depending upon the ultrasound procedure to be accomplished.

In generating the ultrasound signals, the microprocessor 24 pulses a digital signal processor (DSP) 30 to produce the ultrasound signals, at a typical frequency of 3.7 mHz, although this could be within the range of 1-12 mHz. The ultrasound signals are applied to an amplifier 32 and then to transducer 14, which transmits ultrasound signals to the body area of interest. Return signals are directed through the receiving portion of transducer 14 into a time controlled gain (TCG) amplifier 34. The output from TCG amplifier 34 is applied to an analog-to-digital converter 36, which outputs the resulting digital information on twelve output lines 38-38 to the digital signal processor 30, which then directs the data into SRAM memory 44 (static random access memory). An address bus 42 connects microprocessor 22, flash memory 40 and SRAM 44. Flash memory 40 stores the program information.

FIG. 1A shows a generalized system of the present invention utilizing the internet (WWW) 21, a plurality of DCD devices 23-23, which could be either single or multiple module DCDs (as explained in more detail hereinafter), a central database and server 25 and a plurality of IEDs (intelligent electronic devices), including, for example, a PC with a browser 27, a laptop with browser 29, or a PDA with browser 31.

In the overall system, the central database and server 25 connected to the internet 21 has a capability of communicating with a large plurality of DCD devices positioned at various physical locations, such as at various clinics or doctor's offices, each one of which is separately maintained and accounted for by the physician-user at that location. The DCD devices 23-23 may be either a single module device or one with multiple modules. In the system arrangement of FIG. 1A, the cost of an individual DCD is small, particularly compared with a general purpose ultrasound machine, since the DCD can be fairly simple, typically without significant processing power.

The cost of connection to the internet for the DCD, such as through a PDA as shown in FIG. 1 or by some other arrangement, is also quite small. Hence, it is relatively easy for a physician-user to fund his/her part of the system. The processing of the ultrasound image collected by the DCD occurs in the web database server 25. The processed output from database server 25 is then fed back to the practitioner through the internet 21 to the practitioner's IED, which will include conventional browser technology. The ultrasound data collected by the DCDs and transmitted to the web database and server typically will be compressed, as is the information from the web database server 25 back to the individual IEDs.

Figure 4:
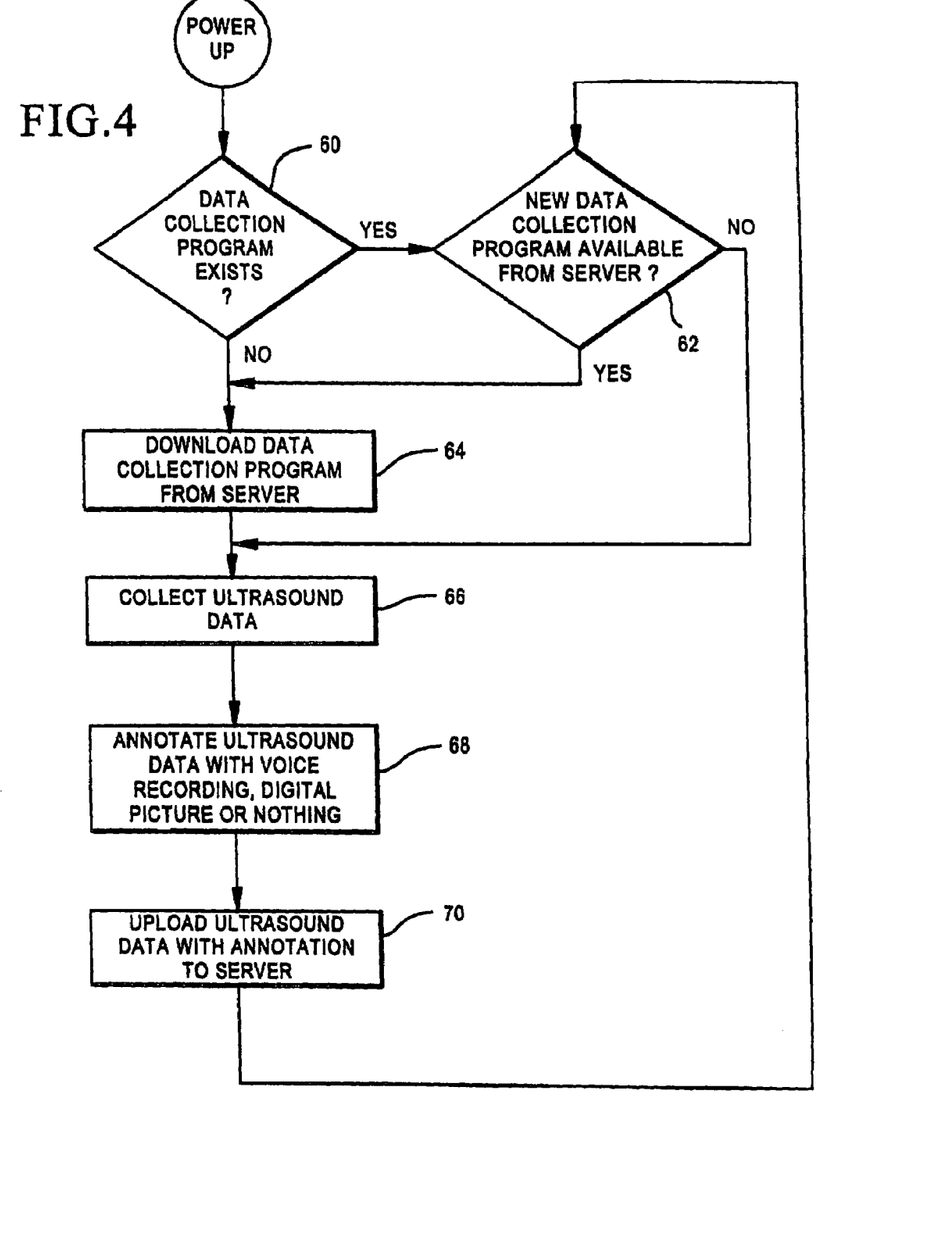
FIG. 4 is a flow chart showing the operation of a portion of the system of the present invention.

A flow chart for downloading the data-collection software into the individual DCD devices as shown in FIG. 4. The data collection software runs in the DCD during the collection of the ultrasound data. It is application-specific, i.e. it is specific to the type of ultrasound procedure being conducted. The web database server maintains a list of software available for each DCD in the system and which are authorized for use by that DCD. Authorization of use of specific software is maintained by appropriate payment by the user of each DCD. The present system permits every DCD instrument to be upgraded or just selected DCD instruments. Once a DCD communicates with the database server for particular software, if new software for that particular application is available, the new software will be loaded into the DCD, if the DCD listed version does not match the overall database software for that specific application.

In the flow chart of FIG. 4, after the DCD is initially powered, a determination is made as to whether or not the particular requested data collection program exists at the server for that DCD. If the data collection program does exist, a determination is then made at block 62 as to whether or not a replacement data collection program is available from the server. If the answer is "yes", or if the requested data collection program does not currently exist in the list for that DCD, the requested data collection program is downloaded from the server (block 64). If the data collection program, on the other hand, does exist in the DCD list and there is no replacement program, then ultrasound data is collected, along with voice (audio) information, typed information and/or digital picture information, if desired, as shown at block 66. The actual ultrasound information is annotated with the additional information (block 68) and then uploaded to the server (block 70) for analysis, as discussed above.

FIG. 3 shows microprocessor 22 controlling a DCD with a total of four identical modules, each with its own transducer. All the modules are served by the microprocessor 22 and the SRAM/flash memory 44, 40. When the modules are ganged together, the field of view being imaged is significantly increased. For instance, a DCD that includes four modules ganged together in a straight line would be appropriate for imaging a narrow but elongated body structure. Larger anatomies, such as the aorta or a third trimester fetus, require even a larger plurality of DCD modules (perhaps a total of 10 modules in three columns) arranged to cover the desired volume. The multiple module DCD, with its corresponding larger field of view, increases the probability of obtaining an image that includes the portion of the body of interest, where some part or feature of the portion of interest may be hidden from view from a single module by shadow structures, such as bowel gas, stones or bone.

The plurality of modules in the DCD are typically operated in parallel so that the total scan time for a multiple module DCD is approximately the same as that for a single module. The transducers in each module have a spatial pattern and orientation (start and stop points) of movement so that their ultrasound signals will not interfere with each other. In some cases, it may be desirable to orient the individual transducers such that one transducer is transmitting while others are receiving relative to the same target. As indicated briefly above, the use of multiple modules, each with a 120° scan angle (as compared to the more typical 75° scan angle), produces more accurate overall images, since the target area is being scanned from more than one position. Such an arrangement produces superior ultrasound data, without the need for a highly skilled device operator.

As an alternative to capture of larger fields of view by use of multiple DCDS, one data collection device could be used to capture 3-D scan cones at different spaced locations in sequence, with the data collected from all of the locations being stored in memory. The plurality of separate data cone information, captured by the single DCD, can then be combined or mosaiced together, using conventional image registration software to create an expanded field of view in three dimensions. The multi-cone data acquisition process is important for properly imaging either large or elongated body portions. It can also be used for imaging of a body portion that cannot otherwise be imaged accurately and completely because of obstruction or shadowing caused by bones or other body parts. In this application, images acquired from three different viewpoints can be registered and combined to provide more accurate and complete information about the structure being viewed. Examples where this is appropriate include imaging of the uterus, including the amniotic fluid therein, which may be obstructed by the limbs of the fetus, and fluid in the lungs, where the ribs occlude the lungs. In the case of the uterus, for instance, images may be acquired at a plurality of locations, e.g. four locations, approximately 6 cm apart, to provide an accurate and complete picture of the uterus.

The ultrasound information gathered by the DCD 12, converted to digital signals and transferred to memory, is then transmitted over a connecting link (Ir link 46 in FIG. 3) to the PDA or similar unit 17 (FIG. 1). It should be understood, however, as indicated briefly above, that other communication links can be used, including various infrared links/protocols, an RF connection or other compliant interface (the "Bluetooth" interface is one example). As indicated above, the PDA 17 is referred to as generally being a "thin" server, which could be a PDA, as indicated, a PC (with Windows software) or any other conventional internet connectable device; even a cell phone having an internet connectability would produce satisfactory results.

The data obtained by the DCD is then sent to the web database server 18 which is connected to the internet. The link between PDA 17 and the internet 16 is by any standard internet access. The database server 18, as indicated above, includes a number of application-specific collection programs which can be downloaded into the DCD through the internet and the PDA.

Once the raw ultrasound data from the DCD 12 is uploaded into database 18, it can be processed in a number of different ways. First, the web database server 18 may include diagnostic software which can itself evaluate the raw data to provide a resulting diagnosis. Further, the database software can create a three-dimensional model of the portion of the body being investigated from the ultrasound information. For instance, in the ultrasound examination of a kidney, a three-dimensional picture of an imaged kidney can be produced, along with any interior stones, which could be shown as interior solid objects. In another example, the abdominal aorta could be shown in three dimensions, along with an indication of the maximum diameter of the aorta.

The resulting processed information from the database server 18 is available to the physician, who has access to the database server 18 through his own PC or similar terminal unit. After review of the information, the physician can then take appropriate action, including, if necessary, instructing the patient to go to the hospital for emergency treatment. Alternatively, the basic ultrasound data could be interpreted at the database server location by an ultrasound technician, or through a combination of processing and skilled interpretation.

In a further embodiment of the present system (FIG. 6), the raw ultrasound data is first processed automatically, in the manner discussed above, at 18. The results of this first automatic analysis are provided to a sonographer/skilled ultrasound technician. The technician reviews the ultrasound data, which includes ultrasound images produced by the automatic processing of the raw ultrasound data and the medical analysis discussed above, referred to in this embodiment together as processed ultrasound information and/or simply processed results. The technician, upon reviewing the processed results, may elect to receive (approve) the processed ultrasound information, or, alternatively, reject the processed ultrasound information, or still further, edit the processed ultrasound information. In the case where the technician accepts the processed ultrasound information, that information, in particular the medical analysis, is sent immediately to the physician, in similar fashion to that described above.

Figure 6:
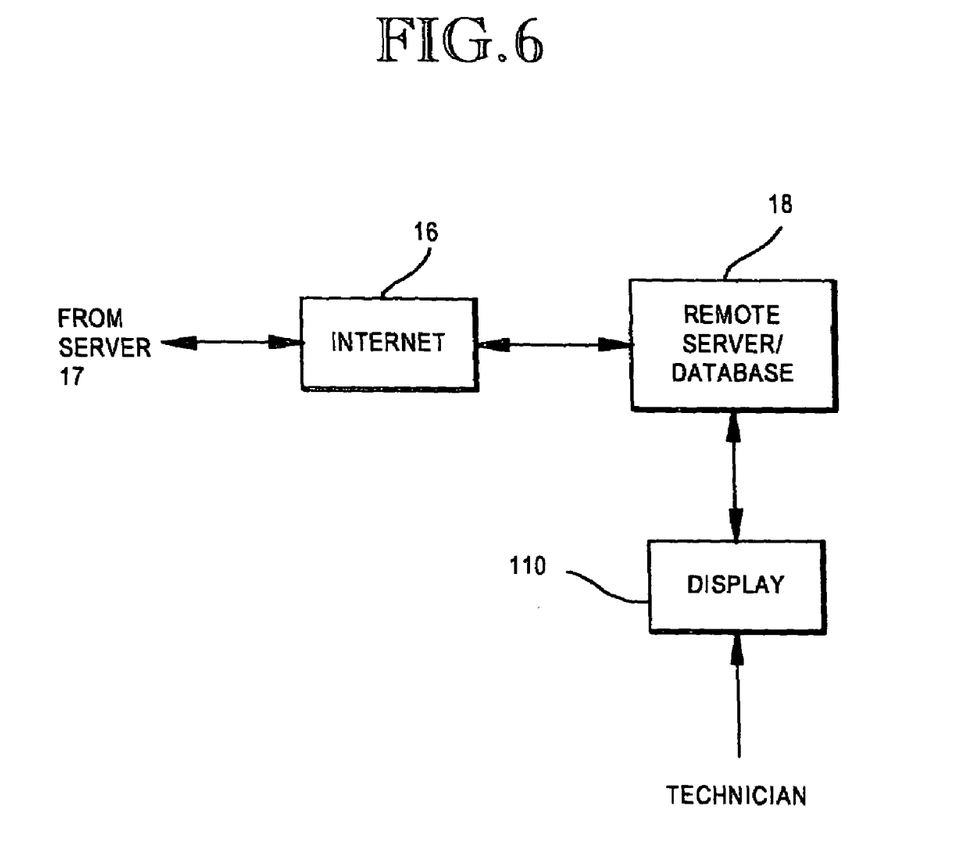
FIG. 6 is a diagram of another embodiment of the system.

If the processed ultrasound information is not accepted, that information is not provided to the physician, although the decision not to accept the information may be transmitted to the physician.

If the technician chooses to edit the processed ultrasound information, that information, in particular the ultrasound image, is provided on a display device 110. When the images (B-Mode or other image) is displayed, the technician may make a number of measurements on the ultrasound images, mark traces which correspond to the outlines of the various anatomical structures displayed, make thickness measurements using calipers, or may make any other marks or measurements of the images. The tracings/measurements are made on the images in the available scan planes, including for example orthogonal scan planes, and are referred to generally as modified processed ultrasound information or modified processed results. That information is submitted to the automatic processing system described above. A new data record is established; the modified processed ultrasound information will then be re-processed. The further results of the processing of the modified processed results are then presented to the physician, who may view the further results, and is free to accept or reject the further results, as indicated above.

Figure 7:
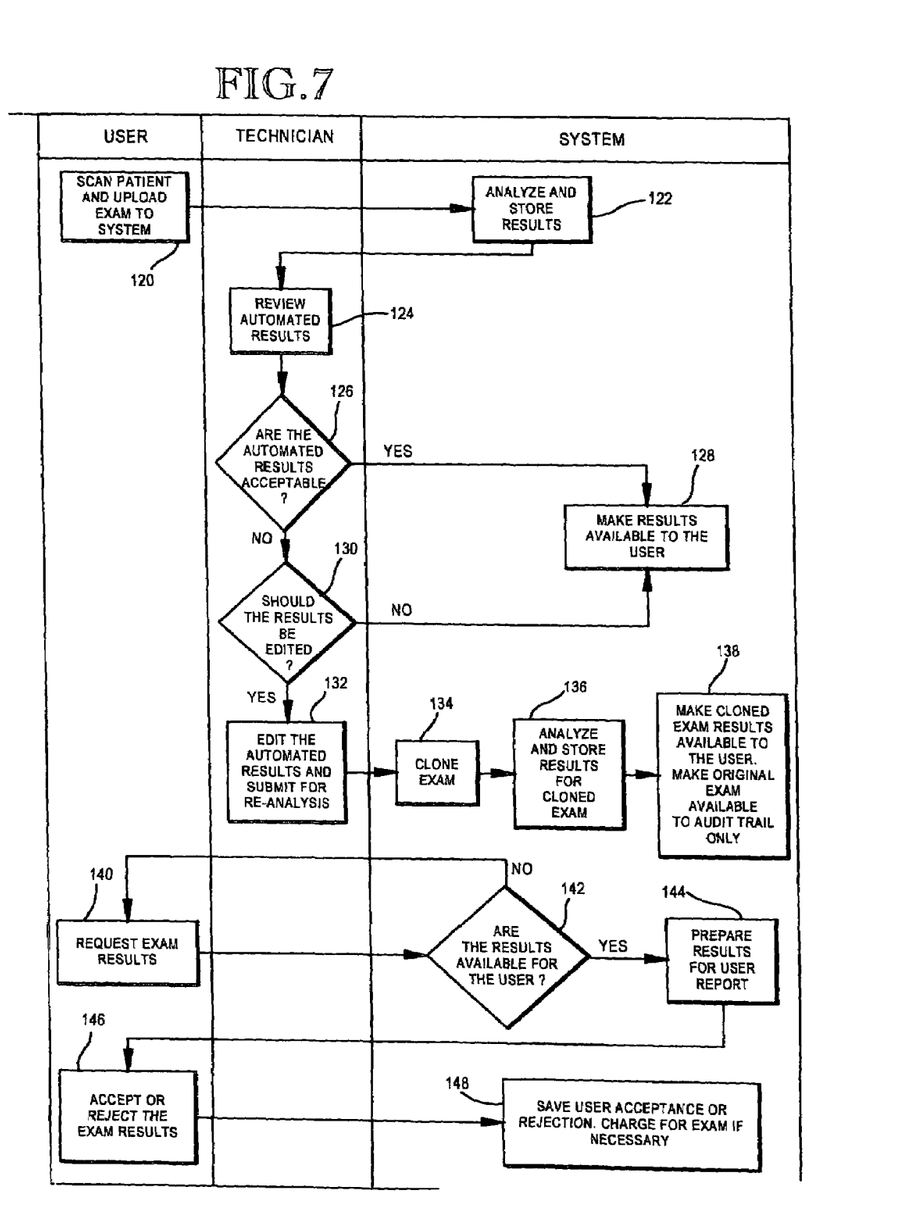
FIG. 7 is a flow chart showing the operational steps of the embodiment of FIG. 6.

FIG. 7 shows the sequence of steps in this embodiment in more detail. First at 120, a patient is initially scanned and the raw ultrasound data is uploaded to the system. The data is then transmitted to the remote location for processing and to produce a medical analysis, with the initial automated results (the ultrasound images and the medical analysis) being stored, as shown at 122. The initial results produced by the automatic processing are then reviewed by an ultrasound technician, as shown at 124. The technician determines, at step 126, whether or not the initial automated results are acceptable. If the initial results are accepted, they are made available to the user (physician) at step 128. If the initial results are not acceptable, then at decision step 130 the technician decides whether or not the initial results should be edited. If the initial results should not be edited, that decision may be communicated to the user, at step 128, although the initial results themselves will not be communicated. In the next step, shown at 132, the initial results of automatic processing (the initial results including in particular the ultrasound image in various modes), is viewed by the technician and the image is marked/traced and/or measurements are taken from the displayed image.

The resulting modified processed ultrasound information is then provided to the processor for repeat (clone) processing and analysis, at steps 134 and 136. The resulting further medical analysis information is then made available to the physician, at step 138.

FIG. 7 also includes the inquiry sequence for the user's browser. The browser makes continuous inquiries, at step 140, as to the availability of results produced by the above process, including the initial results of step 126 and the further results of step 136. If there are no results, as determined at block 142, that information is provided back to the user. If results are available, they are prepared in a user's report, at block 144. The user then, as shown at block 146, has the ability to view the results and then accept or reject the results. The decision concerning acceptance or rejection is then saved by the system, and the charge for the examination is then computed and processed, as discussed in more detail below, at step 148.

The system of the present invention also has a number of additional special features. Referring now again to FIG. 3, the system includes an accelerometer 50 which can be used to detect instrument motion in three-dimensional space. This allows the system to detect and correct for motion introduced if either the operator or the patient inadvertently moves during the ultrasound procedure. In some applications, the accelerometer 50 can be used in monitoring a maximum threshold displacement which may occur during the ultrasound scanning of the patient. If patient movement exceeds the threshold, as determined by the accelerometer, an indication can then be provided to the operator that the scan needs to be re-done. In other applications, the record of motion provided by the accelerometer can be used to orient each individual scan line (the phi scan) with respect to other scan lines. This assures a locked geometry between the successive scan lines.

Accelerometer 50 is sensitive enough to resolve the gravity effect produced by the earth. This allows the system to obtain an indication of the patient's position during the examination. If the patient were supine, with the instrument on the patient's abdomen, the gravity vector would be straight down, normal to the direction of the ultrasound signals. However, even if the position of the patient is known, by means of external information, the earth gravity vector can still provide useful information, e.g. if the patient is supine, and the ultrasound examination is of the patient's bladder, the angle of the ultrasound probe is provided by the gravity vector. The probe angle is important information for a system which does not include the use of a trained sonographer.

In the operational steps of the overall system, which includes the various portions of the system discussed above, an operator first uses the thin server (PDA 17) to access the ultrasound database server 18 through the internet connection. If the patient's record is not in the database, a record is created. The PDA 17 will then provide a list of software available to it from the database for application-specific examinations. The correct one is selected by the operator and the control software for that application then is downloaded into the DCD 12. Once this is completed, the PDA screen will produce a screen image (from the ultrasound web database server 18) with an explanation of how to position the DCD 12 on the patient for the particular selected examination.

The operator then applies a standard coupling gel or gel pad article to the DCD 12 and orients the DCD on the patient, as shown on the PDA 17, and presses the scan button on the DCD 12. The DCD 12 then transmits and collects all of the required ultrasound raw data in a short amount of time, typically two seconds or less.

After the ultrasound data collection is completed, the operator returns DCD 12 to the equipment stand or otherwise positions it in such a way that DCD 12 can communicate via infrared with the PDA 17, and from there to the web database server 18. The uploading of data typically takes a relatively small amount of time, typically less than 45 seconds, and during that time, the operator can locate the patient's record on the database and link the new ultrasound information with the patient's existing record. Once the raw information is in database server 18, it is processed such that it can be readily interpreted by the operator or a physician. The physician will then take appropriate action, if any action is indicated.

In the system of the present invention, a single web database server 18 can respond to many DCDs. The database server 18 will keep a list of software which is available and authorized for each DCD which is connectable to it through the internet. With such an arrangement, the DCD can be a relatively simple, inexpensive, robust device for transmitting and receiving ultrasound data, while the image processing of the data is accomplished by software in the web database server 18, which can serve a large number of similar DCD systems. This minimizes the cost for an individual ultrasound examination carried out with a DCD. The ultrasound data is typically compressed prior to transmission to the web database, which speeds up the transmission and reduces the file storage requirements on the internet server. The processed information can be fed back to the browser with compression as well.

In another specific additional feature, referring again to FIG. 3, a CCD camera subsystem 52 is used with the DCD 12. The CCD camera 52 takes a digital photograph of the patient at the time of the ultrasound procedure. This photograph can be included with the patient's raw ultrasound data in the database. The operator can also take pictures of other important information, such as the patient's insurance card or other insurance information. A video camera can also be utilized as part of the CCD system. The database server 18 can also accept fingerprint or other scan information which aids in patient identification.

In still another feature, again referring to FIG. 3, a microphone and digitizer 54 could be included to record audio information. All audio information during the ultrasound procedure could be recorded, or just selective information provided by the operator.

The audio recording, after it is digitized, can then be readily "attached" or linked to the ultrasound data collected by the DCD and uploaded together to the web-based database server 18. The audio recording can be used at the web server, or can be used along with the processed ultrasound data by the physician-user through an internet connected device. The audio information can provide information concerning the procedure or other information concerning the patient.

Voice-print software can also be included at the web server to analyze the recording and identify the speaker, based on voice print biographical information. This would be another way to both identify the DCD operator and/or the patient.

In some cases, the operator will perform the ultrasound procedure and upload the raw data without necessarily identifying the patient. It is not mandatory that the operator find or create a patient record at the time of the ultrasound procedure. Further, since the ultrasound data will be stored in memory, there can be a lapse between the time of the ultrasound procedure and when the raw data is uploaded. When the raw data is uploaded, either shortly after the data is obtained or at a later time, an "exam incident" indicator can be created in database 18, which includes the exact time and date the procedure was performed, as well as the serial number of the device used. Database 18 will eventually be able to link the DCD instrument to a specific location and a list of possible users. When convenient, the operator will access the database, where the list of "exam incidents", connected with their facility/user name, is listed. The operator can then connect the appropriate patient to the exam.

The present invention has a number of applications in addition to the ability to provide ultrasound procedures quickly, efficiently and at a low cost. First, the database has the capability of maintaining and collecting every ultrasound examination on every patient in the database. This provides an ability to track a patient's history over time. For instance, by maintaining a complete history of all abdominal aorta scans, the system can provide an indication on the progression and growth of an aneurysm in the aorta. The data can even be presented in the form of a computer-generated video or movie of the characteristics of the particular organ changing over time. This visual information may also be a significant incentive for the patient to follow guidelines suggested by the physician.

The system also provides to the clinician an ability to "blind" clinical studies early in an application product design cycle. Raw data for a particular ultrasound examination can be collected in the course of normal patient flow. When a surgeon or other physician is treating a particular condition, they will take an ultrasound scan at the same time that a conventional CT or MRI examination is ordered. The radiologist or other professional interprets the results of the CT or MRI in normal course. An analysis of the ultrasound data is then also performed. The results can then be compared and a report generated concerning the correlation between the ultrasound results and the more conventional CT or MRI results.

One of the significant advantages of the present invention is the resulting relatively low cost to the physician, and to the patient, of an ultrasound examination. The DCD and PDA hardware are quite inexpensive compared to a traditional ultrasound machine. The charge made by a central system administrator for managing the database would also be relatively inexpensive. The actual cost would depend upon the processing necessary for a particular ultrasound procedure. The present system can also be used to develop appropriate billing for the patient's insurance provider, saving time and expense for the insurer.

Figure 5:
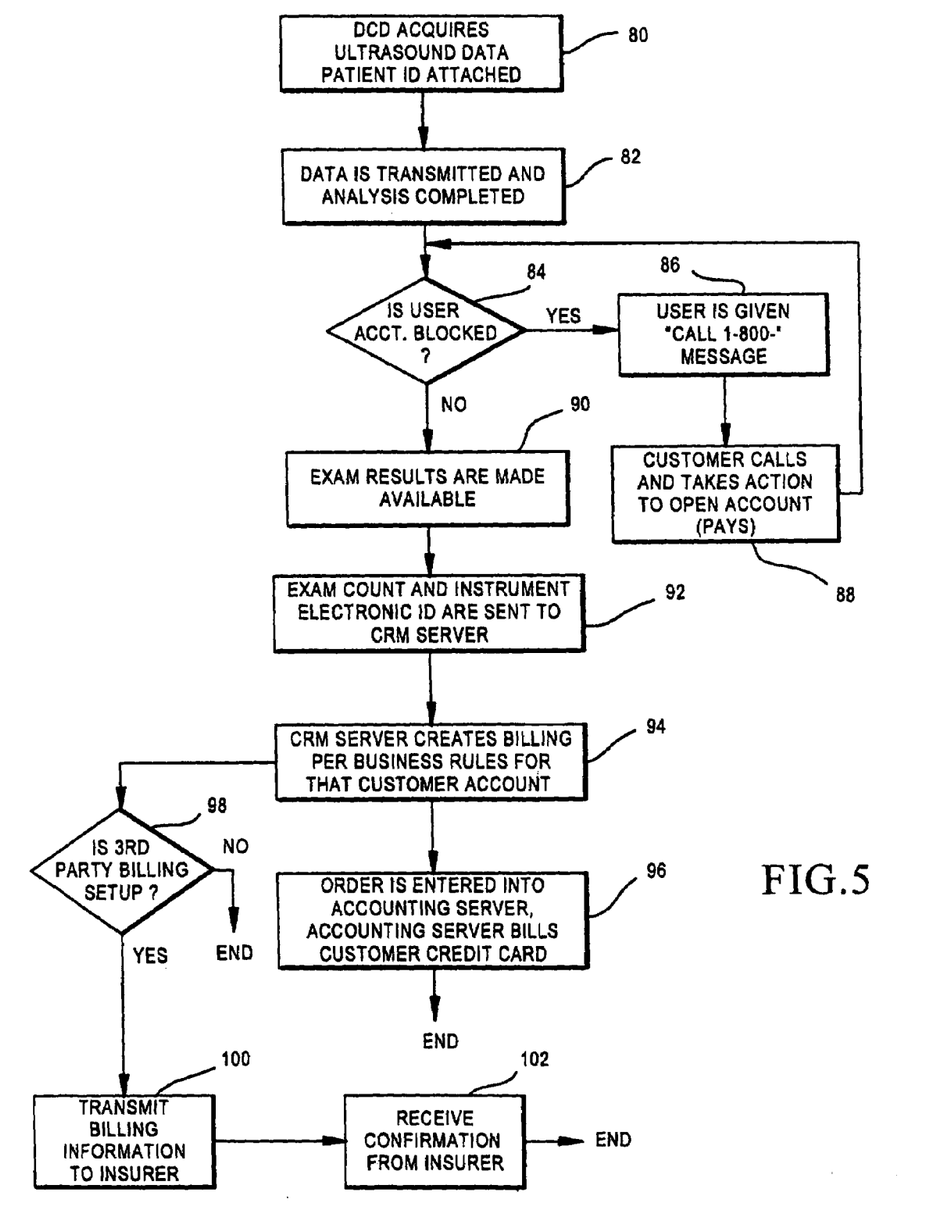
FIG. 5 is a flow chart showing steps in a business method aspect of the present invention.

FIG. 5 shows a business payment system or method involving use of the remotely based ultrasound system of the present invention. In block 80, the acquiring event is shown, i.e. the ultrasound data is acquired by a user (typically a physician) using a DCD. The particular ID (identification) of the patient is attached to that data. In block 82, the data is transmitted (uploaded) to the internet and then to the database server, where it is processed as discussed above. After processing is completed, it is then determined at block 84 whether the user's account is "blocked" and thereby prevented from receiving analysis information. If "yes", the user is provided a message to call a particular phone number or similar contact, at block 86.

The user then has the opportunity to take any action to re-open the account (block 88). The user's account will be blocked typically by an unpaid balance. If the user's account is not blocked, or is reopened by action of the user, the results of the processing are made available to the user, as shown at block 90.

After the results are made available to the user, both the identification number of the examination and the ID of the particular electronic instrument used are sent to the customer relationship management (CRM) accounting server, as shown at block 92. The CRM server then creates a billing for that user's account in accordance with the contract between the user and the system owner (block 94); the CRM server either bills the user's credit card or provides a statement for payment to the user, as shown in block 96. This is the end of the billing system relative to the user directly.

There is also a determination made by the accounting server as to whether a third party (insurance company) is to be billed for the service, as shown at block 98, which is a branch of the program. If not, the third party billing branch ends. If there is to be a third party billing, billing information is transmitted to the third party insurer, as shown at block 100. A confirmation of receipt is then received from the insurer (block 102).

The overall business billing system includes coordination between the analysis and transmission of the ultrasound data and the determination of the status of the user's account. If the user's account is current, then the billing is automatically tallied and provided both to the user and/or to the insurance company, as appropriate.

Hence, an ultrasound system has been developed which combines relatively inexpensive data collection hardware at a physician's site with a remote processing and evaluation capability available to the physician by means of a web database server. The processing can be relatively inexpensive, with the result, such as a three-dimensional model, being made available to the physician for evaluation. In such an arrangement, the physician, without specialized ultrasound training, can readily make accurate diagnostic determinations from the results provided. A specialist in ultrasound interpretation is not necessary. Hence, the system is a general purpose, application-specific structure where the system performs in operation like an application-specific device, but has the capability, depending upon the program software, of operating and processing data like a plurality of different application-specific structures, using the same hardware and software base but with different program applications obtained from a central database.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A system for producing medical results using application-specific medical ultrasound information, comprising:

a local ultrasound data collection assembly to carry out an ultrasound scan of a selected part of the human body of a patient at a given location and to produce raw, substantially unprocessed ultrasound information therefrom;

a data transmission system for transmitting said substantially unprocessed ultrasound information produced by the data collection assembly to a processing location physically remote from the data collection assembly location;

a processor at the remote location for automatically processing said transmitted information sufficiently to produce initial medical results comprising ultrasound images and/or a medical analysis of the selected body part from the raw ultrasound information, wherein the initial medical results are then transmitted to a sonographer who accepts the initial medical results, rejects them or decides to edit them, wherein if accepted, the initial medical results are transmitted to a medical practitioner associated with the patient; and a display device for displaying the ultrasound images, having the capability of permitting the sonographer to take measurements of the ultrasound images and/or mark portions of the images to produce edited ultrasound images, wherein the edited ultrasound images are then transmitted to the processor for another automatic processing thereof to produce further medical results, the further medical results being then transmitted to the medical practitioner associated with the patient.

2. A system of claim 1, wherein the ultrasound data collection assembly carries out a plurality of ultrasound scans of the selected body part at different locations, and wherein the processor includes means for combining the plurality of ultrasound scans together into a combined ultrasound image.

3. A system of claim 1, wherein the processor performs the same automatic processing function on the medical analysis as on the raw ultrasound information.

4. A system of claim 1, wherein if the medical analysis is rejected by the sonographer, the medical analysis is not communicated back to the medical practitioner, although the decision of the sonographer to reject the medical analysis is communicated to the medical practitioner.

5. A method for producing medical results using application-specific medical ultrasound information, comprising the steps of:

carrying out an ultrasound scan of a selected part of the human body at a given location and producing raw, substantially unprocessed ultrasound information therefrom;

transmitting said raw ultrasound information to a processing location physically remote from the data collection assembly location;

automatically processing said transmitted information sufficiently to produce initial medical result information comprising ultrasound images and/or a medical analysis of the selected body part from the raw ultrasound information;

displaying the ultrasound images and/or the medical analysis for review by a sonographer;

transmitting the processed ultrasound information to a medical practitioner associated with the patient if the sonographer accepts the initial medical result information;

permitting the ultrasound images to be edited by the sonographer for enhancement or detailing of the images to produce edited ultrasound images;

automatically processing the edited ultrasound images to provide further medical results; and transmitting the further medical results to a medical practitioner associated with the patient.

6. The method of claim 5, wherein unacceptable medical results are not transmitted back to the medical practitioner, but the decision to reject the medical results is so transmitted.

* * * * *